United States Patent [19]

Johnston et al.

[11] Patent Number: 4,650,673

[45] Date of Patent: Mar. 17, 1987

[54] ORAL IMMUNIZATION OF MAMMALS

[75] Inventors: David Johnston, Maple; Kenneth F. Lawson, King City, both of Canada

[73] Assignee: Connaught Laboratories Limited, Willowdale, Canada

[21] Appl. No.: 773,543

[22] Filed: Sep. 9, 1985

[51] Int. Cl.$^4$ ................... A01N 25/00; A61K 39/28
[52] U.S. Cl. ........................ 424/84; 424/88; 424/89; 424/92
[58] Field of Search ............ 424/89, 92, 88, 84

[56] References Cited

U.S. PATENT DOCUMENTS

| | | | |
|---|---|---|---|
| 4,014,991 | 3/1977 | Baer et al. | 424/89 |
| 4,040,904 | 8/1977 | Slater | 424/89 X |
| 4,320,115 | 3/1982 | Bijlenga | 424/89 |

FOREIGN PATENT DOCUMENTS 0100752  8/1982  European Pat. Off. .

OTHER PUBLICATIONS

Can. Vet. Jour., vol. 14, No. 9 (1973) Black et al, pp. 206–211.
Can. J. Comp. Med. 34 (1970) Black et al, pp. 309–311.
American Journal of Epidemiology, 93, No. 6 (1971) Baer et al, pp. 487–490.
American Journal of Epidemiology, 96, No. 3 (1972) Debbie et al, pp. 231–235.

*Primary Examiner*—Howard E. Shain
*Attorney, Agent, or Firm*—Sim & McBurney

[57] ABSTRACT

A composition and method for immunizing carnivores and other mammals, especially foxes, against rabies and other pathogenic diseases, by setting out and orally administering a dose of a vaccine, are described. The vaccine is enclosed in a bite-permeable sponge-like vector and the container is coated with a membrane containing an attractant, such as tallow. The method operates by penetration of a sponge resulting in distribution of relatively large volumes of vaccine to the oropharyngeal cavity of the mammals.

22 Claims, No Drawings

ORAL IMMUNIZATION OF MAMMALS

FIELD OF INVENTION

The present invention relates to the dissemination of an oral vaccine for the vaccination of mammals against pathogenic disease, particularly rabies.

BACKGROUND TO THE INVENTION

Rabies is a major public health problem in many countries, especially those in the developing areas, and the control of rabies in animals, and especially in wild carnivores, such as the fox, is integral to the ultimate goal of minimizing the public health significance of this disease. Population reduction of the animals, which has been practiced in the past, has not proved to be an effective wild rabies control technique and the vaccination of carnivores associated with the disease has received increasing interest in recent years.

There have been a number of previous attempts to vaccinate carnivores through the oropharyngeal cavity. Black and Lawson (Can. Vet. J. 14[9], 206, [1973]) were able to orally vaccinate foxes, both silver and red, utilizing the ERA (Trademark) strain of rabies virus grown in primary porcine kidney cells, by introducing the vaccine into the oropharyngeal cavity. The virus utilized in this case was lyophilised and specially set out as "free choice" for the animals to eat. The use of bait is mentioned in this publication, but no description is given as to the type of bait. Black et al [Can. J. Comp. Med., 34, 309 (1970)]indicated methods of oral vaccination by stomach tube and Baer et al (Am. J. Epid. 93, 487 [1971]) indicated in their publication, methods of oral vaccination for grey and red foxes by various routes, such as stomach tube, feeding explosion using a "coyote-getter", and other methods. These authors did not attempt to use baits to disseminate the vaccine. Baer and Winkler (U.S. Pat. No. 4,014,991) disclose the use of a sausage containing vaccine held in a plastic tube inside the sausage as a bait. Debbie et al (Am. J. Epid., 96, 231, [1972]) showed that wild red foxes may be successfully vaccinated by the oral route using an ERA type of vaccine with a titre $>10^{3.4}$ mouse intracerebral lethal dose 50 ($MICLD_{50}$)/0.03 ml. Steck in published European Patent Application No. 0100752 discloses the use of a high titre vaccine within a container placed in chicken heads as bait for carnivores.

Such prior art procedures suffer from a number of drawbacks in that they require capturing the foxes for administration of the vaccine, the use of high titre unlicensed vaccines and/or permit the administration of only low volumes of vaccine. There exists, therefore, a need for an effective manner of oral administration of vaccines to mammals.

SUMMARY OF INVENTION

In accordance with the present invention, there is provided a novel baited immunizing composition capable of oral administration to mammals, comprising a bite-permeable sponge-like vehicle or vector having a vaccine-impermeable coating thereon of an attractant for the mammal and having an immunization agent against a pathogenic disease absorbed therein.

The mammal is attracted to the baited composition by the attractant. Upon bite penetration of the coating, the sponge is squeezed thereby expelling the vaccine to the mouth of the mammal, thereby distributing the vaccine to the oropharyngeal mucosa of the mammal. Since a highly-absorbent material is used as the vector, large volumes of vaccine can be held within the composition and are administered to the mammal upon bite penetration.

The novel compositions of the invention may be prepared by any convenient procedure. In one embodiment of the invention, baited immunizing compositions are formed by a method which comprises providing an absorbent sponge-like vehicle or vector, coating the exterior surface of the vector with a vaccine- impermeable mammal-attractant material, injecting a liquid immunization agent against a pathogenic disease into the vector through an injection opening in the vaccine-impermeable material to be absorbed by said vector. The compositions of the invention can conveniently be lyophilised for long term storage.

The immunization agent may be orally administered to mammals using the composition of the invention by distributing a plurality of individual baited compositions in an area inhabited by the mammals, so that the immunization agent is orally administered in the required dose upon bite penetration of the vector by the mammal.

The present invention is particularly effective and useful in the immunization of wild carnivores, especially foxes, against rabies and the present invention will be described in more detail below with respect thereto. However, it will be understood that the principles of the present invention are applicable to the immunization of a wide variety of wildlife population and other mammals, such as dogs, against a wide variety of pathogenic disease.

DESCRIPTION OF PREFERRED EMBODIMENTS

The rabies vaccine which is used in the present invention may be a licensed liquid rabies vaccine, such as the commercial ERA vaccine. The ERA vaccine is an attenuated virus, has been licensed and has been used extensively for anti-rabies treatment of domestic animals. The potency of this vaccine exhibits some tendency to decrease at elevated temperatures above about 20° C. In order to ensure retention of potency in the field during periods of higher temperatures, an effective amount of a stabilizer, such as egg yolk or other known stabilizer, may be added to the vaccine, permitting use at higher temperatures, typically up to about 27° C. In addition, the vaccine in the compositions, in stabilized or non-stabilized form, may be freeze-dried after formation for storage without loss of potency. The freeze-dried compositions may be reconstituted when ready for distribution.

The vaccine is employed in a volume and at a titre that enables an effective amount of the rabies vaccine to be orally administered to the carnivore. The sponge size may be tailored to incorporate the desired volume of vaccine considered efficacious. The sponge preferably is substantially saturated with liquid vaccine so as to expel the significant volumes of the vaccine upon bite penetration.

The use of a licensed liquid vaccine or licensed lyophilized vaccine which is reconstituted to liquid form is preferred, since considerable work has usually been performed on the general safety of such vaccines. Most of such vaccines are at present of a lower titre than some of the experimental vaccines that have been employed for oral vaccination. Relatively large volumes of vaccine can be delivered using the present invention in contrast to those achievable by prior art techniques (see U.S. Pat. No. 4,014,991 Baer et al and European Patent Application No. 0100752).

We have determined that a cube of approximately 1¼ inches square is an effective size for distribution of rabies vaccine in the environment and that the cubic shape makes for more ready handling of these baits both in production and dissemination. The vector, being a sponge-like material, retains the vaccine and is bite-permeable so that the vaccine can be squeezed from the interior of the vector, to be lodged in the mouth or oropharyngeal mucosa of the mammal, such as a fox. Since the vector containing the vaccine is also the bait, there is less likelihood of loss of vaccine when the mammal bites into the vector. The sponge-like property of the vector also allows for the retention of the vaccine and prevents spillage, this in contrast to the other methods of vaccine containment described in the prior art which once bitten can allow the liquid to spill before entering the buccal cavity, or can become dislodged from the body of the bait as may occur with chickenheads.

The baited compositions of the invention may be formed as follows. The sponge-like vector may be coated, in one or a plurality of steps, with a liquid non-permeable coating such as histological wax containing an attractant, such as beef-fat, and is then filled with vaccine using a suitable needle. A liquid non-permeable coating is important to avoid undue washing away in the field. The liquid vaccine is absorbed into the pores of the sponge-like vector. The opening resulting in the vector surface from the invention is then stopped by a further application of the non-permeable coating. The resulting composition may be frozen for storage purposes.

When used in the field, the vector may be shaken in a plastic bag to which liver slurry is added to act as a further attractant for mammals. Obviously any other such additional attractant can be employed.

In use of the compositions of the invention for immunization, the vaccine-containing bait is set out for the fox or other wild carnivores, conveniently by dropping from the air, and the fox receives the vaccine by biting through and squeezing the vaccine from the sponge allowing contact between the vaccine and the tongue and the oropharyngeal mucosa. The biting action by the carnivore on the sponge, therefore, releases an immunizing dose of the vaccine into the tongue and cheek mucosa and oropharyngeal cavity of the fox, which is thereby immunized against rabies virus.

EXAMPLES

Example 1

This Example illustrates the formation of bait compositions in accordance with the invention.

Sponges, made of a synthetic material, were provided in the form of a 1¼×1¼×1½ inch cube. The sponges were coated four times by dipping into a hot mixture (65° to 70° C.) of a material which contained about 33% beef fat and about 67% histological wax. After cooling to room temperature, the coated sponges were irradiated and stored sterile at 4° C. until needed. Approximately 14 ml of ERA rabies vaccine was placed in the coated sponges using a 13 gauge needle attached to a delivery system. The beef-fat/wax mixture was used to seal the hole left in each of the sponges by the dispensing needle. The baits were stored frozen at −30° C., were found to have a shelf life of at least seven months.

Example 2

This Example illustrates the propagation and stabilization of ERA rabies vaccine.

The ERA strain of rabies virus was propagated in primary porcine kidney tissue culture in the presence of Hanks' salts with 0.5% lactalbumin and supplemented with normal bovine serum. After infection of the tissue culture, viral harvests were obtained on days 7 through 14. The harvests were pooled, a stabilizer added and frozen at −30° C. The vaccine so produced had a viral titre of $10^{5.5}$ to $10^{6.3}$ ($MICLD_{50}$) per 1 ml.

The potency of this commercial ERA vaccine normally can drop when held in the liquid state at temperatures between 21° and 25° C., as shown by the results in the following Table 1:

TABLE 1

RESULTS OF TESTING ERA VACCINE

| TIME (DAYS) | POTENCY[a] OF VACCINE HELD AT | |
|---|---|---|
| | −30° C. | R.T.[b] |
| 6 | 5.4 | 4.2 |
| 10 | 5.3 | 3.7 |
| 14 | 5.3 | 3.4 | notes:
[a]Fluorescent Antibody Titre/ml.
[b]Room Temperature, 21° to 25° C.

The addition of 10% v/v egg yolk, however, was found to increase the stability of the vaccine in the liquid state, as shown by the results, in the following Table 2:

TABLE 2

ADDITION OF STABILIZER TO VACCINE
STABILITY RESULTS (FAT[1]/ml)

| STABILIZER ADDED | 6 DAYS | | 13 DAYS | |
|---|---|---|---|---|
| | FROZEN CONTROL | SAMPLE AT ROOM TEMP. | FROZEN CONTROL | SAMPLE AT ROOM TEMP. |
| 10% egg yolk | 5.7 | 5.3(+0.3)[2] | 6.0 | 4.8(+1.0)[2] |
| None | 5.7 | 5.0 | 6.2 | 3.8 | notes:
[1]FAT = Fluorescent Antibody Titre
[2](increased stability $log_{10}$).

The stabilized vaccine was used to form baits following the procedure of Example 1.

Example 3

This Example also illustrates the propagation of ERA rabies vaccine.

The ERA strain of rabies virus was propagated in the BHK21 13S cell line. The supporting media was modified Earles salts containing 10% tryptose phosphate broth, 1% L-glutamine supplemented with fetal calf serum and adjusted to pH 7.5. After infection of the tissue culture, viral harvests were obtained on days 3 through to 5. Stabilizers were added to the harvested fluids, as described in Example 2, which were stored frozen at −30° C. The vaccine so produced has a viral titre of approximately $10^{7.1}$ $MICLD_{50}$ per 1 ml.

Example 4

This Example illustrates the stabilizing of ERA rabies vaccine.

A regular lot of bulk ERA vaccine was suspended in previously coated sponges following the procedure described in Example 1. The vaccine baits were placed in a lyophilizer and freeze-dried over a 7 day cycle. The freeze-dried baits were reconstituted at the end of that period with distilled water and tested for viral potency by the fluorescent antibody test. The results are reproduced in the following Table 3, which show the vaccine to have a good viral recovery and stability.

TABLE 3

LYOPHILIZATION OF ERA RABIES VACCINE IN BAITS

| | POTENCY FAT/ml | |
|---|---|---|
| SAMPLE | FROZEN BAIT | LYOPHILIZED BAIT |
| 1 | 5.6 | 5.6 |
| 2 | 5.4 | 5.5 |

Example 5

This Example illustrates the immunization of foxes using the compositions of the invention.

Twenty red foxes (Vulpes vulpes) born and reared in captivity with no known prior exposure to rabies virus were divided into two groups, 10 foxes per group. Group one received one bait each, containing 10 ml of commercial ERA vaccine with a titre of $10^{6.1}$ MICLD$_{50}$ and prepared following the procedure of Example 1, while group two, the control group, received no vaccine baits. All baits were completely consumed within 3 hours after being placed in the fox cages of group one. A careful check of the cages did not show any evidence of vaccine spill. The animals were bled at days 0, 30 and 90 in order to determine their serological profile. Serum neutralizing rabies antibody was measured by the Rapid Focus Forming Inhibition Test (RFFIT). All animals were observed daily for signs of illness or behavioral changes. The foxes were challenged with virulent rabies virus 90 days after vaccination. The rabies virus used to test or challenge immunity was a suspension of rabies positive fox salivary glands. Titre of the challenge virus was $10^{7.3}$, MICLD$_{50}$ per ml. The challenge dose administered to each fox was approximately 100 fox LD$_{50}$ and was administered as a 2 ml dose in the biceps femoris muscle.

All animals were observed for a period of 90 days after challenge, at which time the survivors were killed. Brain tissues from each animal were tested for the presence of infectious rabies virus by the rabies fluorescent antibody test. Five of ten vaccinated foxes showed a significant antibody response at day 28 post-oral vaccination. On challenge, 5 of the animals showing an antibody response resisted challenge while 10 of 10 untreated animals succumbed to rabies within 36 days post-challenge. The brains of all animals which died on challenge were identified as rabies positive by the fluorescent antibody test. The brains of the surviving animals were rabies negative by the F.A. test.

The results of the challenge by the rabies street virus demonstrates the value of the antibody as a measure of vaccine efficacy.

Example 6

This Example illustrates the effect of vaccine potency on antibody levels. Thirty-eight red foxes, as previously described, were divided into four groups, 8 to 10 foxes per group and were treated as follows:

Group 1: Each fox was fed one bait containing 14 ml of a commercial ERA vaccine with a titre of $10^{6.1}$ MICLD$_{50}$ Group 2: Each fox was fed one bait containing 14 ml of a commercial ERA vaccine with a titre of $10^{5.3}$ MICLD$_{50}$ Group 3: Each fox was fed one bait containing 14 ml of a commercial ERA vaccine with a titre of $10^{4.4}$ MICLD$_{50}$ Group 4: Each fox was fed one bait containing 14 ml of a commercial ERA vaccine with a titre of $10^{4.2}$ MICLD$_{50}$ In each case, the baits were produced following the procedure of Example 1.

The animals were bled at days 28 and 56 post-oral vaccination and serum neutralizing rabies antibody was measured by RFFIT. All the animals were observed daily for signs of illness or behavioral changes over a period of 90 days. None of the animals showed symptoms of rabies as a result of vaccination over the 90 day observation period. The serological profile obtained is reproduced in Table 4 below. The protective dose 50 in foxes on this test is $10^{4.6}$ MICLD$_{50}$.

TABLE 4

RESULTS OF DOSE RESPONSE IN FOXES

| TITRE[a] OF VACCINE | FOX NO. | RESULTS[b] DAY 0 | DAY 28 | TITRE[a] OF VACCINE | FOX NO. | RESULTS[b] DAY 0 | DAY 28 |
|---|---|---|---|---|---|---|---|
| $10^{6.1}$ | 664 | neg | 40.4 | $10^{4.4}$ | 831 | neg | neg |
| | 889 | neg | 8.98 | | 876 | neg | neg |
| | 882 | neg | 13.0 | | 901 | neg | neg |
| | 1110 | neg | 31.2 | | 829 | neg | 6.72 |
| | 838 | neg | neg | | 747 | neg | neg |
| | 867 | neg | 21.8 | | 806 | neg | neg |
| | 871 | neg | 9.24 | | 1043 | neg | 0.35 |
| | 1050 | neg | 13.5 | | 1116 | neg | 3.39 |
| | 1033 | neg | 3.65 | | 1102 | neg | 3.96 |
| | 1100 | neg | 23.0 | | 1076 | neg | neg |
| | | | (9/10)[c] | | | | (4/10)[c] |
| $10^{5.3}$ | 887 | neg | 13.2 | $10^{4.2}$ | 906 | neg | neg |
| | 649 | neg | 39.1 | | 837 | neg | neg |
| | 912 | neg | died | | 858 | neg | neg |
| | 842 | neg | neg | | 803 | neg | neg |
| | 850 | neg | 49.9 | | 802 | neg | neg |
| | 832 | neg | 4.22 | | 1117 | neg | neg |
| | 765 | neg | 5.6 | | 1026 | neg | neg |
| | 1129 | neg | 18.0 | | 1113 | neg | neg |
| | 1078 | neg | 0.83 | | | | (0/8)[c] |
| | 1025 | neg | neg | | | | |

TABLE 4-continued

| RESULTS OF DOSE RESPONSE IN FOXES | | | | | | | |
|---|---|---|---|---|---|---|---|
| TITRE[a] OF VACCINE | FOX NO. | RESULTS[b] DAY 0 | DAY 28 | TITRE[a] OF VACCINE | FOX NO. | RESULTS[b] DAY 0 | DAY 28 |
| | | (7/9)[c] | | | | | | notes:
[a]Titre recorded as MICLD$_{50}$/1 ml
[b]Recorded as international units/ml
[c]Number with antibody/number vaccinated by bait As may be seen from the results of Table 4, the potency of the vaccine has a direct influence on the number of animals showing rabies antibody levels.

Example 7

This Example shows the effect of the compositions of the invention on dogs.

Each of six rabies sero-negative dogs were given one vaccine bait containing 14 ml of the ERA rabies virus propagated in the BHK21 13S cell line, in accordance with the procedure of Example 3, with the baits being prepared following the procedure of Example 1. The vaccine had a titre of $10^{7.1}$ MICLD$_{50}$/1 ml. The dogs consumed the bait within 3½ hours. Blood samples were taken pre-vaccination and at days 7 and 28 post-oral vaccination for rabies serum antibodies as determined by RFFIT. The results obtained are set forth in the following Table 5, from which it can be seen that all six dogs responded with significant antibody levels.

TABLE 5

| ANTIBODY LEVELS OF DOGS VACCINATED WITH BAIT CONTAINING ERA/BHK 21 | | | |
|---|---|---|---|
| DOG NUMBER | ANTIBODY LEVELS RFFIT* | | |
| | DAY 0 | DAY 7 | DAY 28 |
| 47 | 0 | 0.5 | 2.0 |
| 48 | 0 | 0.35 | 0.63 |
| 49 | 0 | 0.5 | 1.35 |
| 50 | 0 | 0.23 | 0.66 |
| 51 | 0 | 0.47 | 11.3 |
| 53 | 0 | 0.45 | 4.19 | note:
*International Units per 1 ml

Example 8

This Example illustrates the use of the compositions of the invention in the wild.

In 1984 a large-scale (552 km$^2$) field trial was initiated in Huron County, Ontario, Canada to test the acceptance of the sponge baits by wild carnivores. The parameters of this trial are given in the following Table 6:

TABLE 6

| PARAMETERS OF CANADIAN FIELD TRIAL | |
|---|---|
| PARAMETER | VALUE |
| Size of baited area | 552 km$^2$ |
| Number of baits dropped | 9,984 |
| Number of km flown in area | 576 km |
| Density of baits/km flown | 17.3 |
| Density of baits/km$^2$ | 18.1 |

In this field trial tetracycline hydrochloride was used in the baits as a marker to indicate bait ingestion rather than a vaccine. Tetracycline was applied as part of the last coating in an amount of about 450 to 500 mg/bait. Deposits of tetracycline can be seen in the teeth of animals ingesting the bait when thin sections of teeth are viewed under an ultraviolet microscope. The presence of such deposits on the teeth of captured animals, therefore, was an indication that the animal had eaten the bait. With the exception of the substitution of tetracycline hydrochloride for the rabies vaccine, the baits were produced following the procedure of Example 1.

In total, 211 animals were recovered from the baited area by local trappers and the analysis of these specimens is shown in the following Table 7:

TABLE 7

| INGESTION RATES OF SELECTED CARNIVORES | | |
|---|---|---|
| SPECIES | SAMPLE SIZE | % EATING BAITS |
| FOX | 89 | 64 |
| SKUNK | 56 | 34 |
| RACCOON | 66 | 24 |

These ingestion rates are within the range found in similar trials using beef meatballs as bait. The results in Table 7 indicate that the sponge bait is as acceptable as other known baits in reaching a significant percentage of the wild carnivore population.

SUMMARY OF DISCLOSURE

In summary of this disclosure, the present invention provides a novel manner of immunization of a variety of animals, particularly carnivores against rabies, by the use of a baited sponge which contains a liquid immunizing vaccine. Modifications are possible within the scope of this invention.

What we claim is:

1. An immunization composition capable of oral administration to mammals, comprising a bite-permeable highly-absorbant sponge-like vehicle capable of absorbing a liquid immunizing agent therein and of expelling said liquid immunizing agent therefrom upon compression of said vehicle, said vehicle having thereon an immunizing agent-impermeable coating of an attractant for the mammal and having a liquid immunizing agent against a pathogenic disease absorbed therein.

2. The composition of claim 1 wherein said immunizing agent is capable of immunizing a carnivore against a pathogenic disease.

3. The composition of claim 1 wherein the immunizing agent is attenuated rabies vaccine.

4. The composition of claim 3 wherein the rabies vaccine is stabilized for storage by lyophilization of the vehicle.

5. The composition of claim 3 wherein the rabies vaccine is stabilized for higher temperature use by the addition of a stabilizer containing egg yolk.

6. The composition of claim 1 wherein the attractant is contained in a histological wax provided as a nonpermeable coating on the vehicle.

7. The composition of claim 6 wherein the attractant is beef-fat.

8. The composition of claim 1 wherein the sponge-like vector has a generally cubic shape.

9. The composition of claim 3 wherein the vaccine is commercial ERA vaccine.

10. The composition of claim 3 wherein the vaccine is an ERA vaccine grown on the $BHK_{21}$ cell line.

11. A method of preparing an immunizing composition, which comprises:
   providing a highly-absorbent sponge-like vehicle capable of absorbing a liquid immunizing agent therein and of expelling said liquid immunizing agent therefrom upon compression of said vehicle,
   coating the exterior surface of the vehicle with an immunizing agent-impermeable attractant material, and
   injecting a liquid immunizing agent against a pathogenic disease into the vehicle through an injection opening in the vaccine-impermeable material to be absorbed by said vehicle.

12. The method of claim 11 wherein said liquid immunizing agent is injected into the vehicle in a volume sufficient to substantially saturate the vehicle.

13. The method of claim 11 including freezing the composition for storage.

14. The method of claim 11 wherein the liquid vaccine is injected into the vehicle in a volume which approximates the absorptive capacity of the vehicle.

15. A method or orally administering a liquid immunizing agent to a mammal, which comprises setting out a baited composition comprising a bite-permeable highly-absorbant sponge-like vehicle capable of absorbing the liquid immunizing agent therein and of expelling the liquid immunizing agent therefrom upon compression of said vehicle, said vehicle having thereon a coating of an attractant for the mammal and having a liquid immunizing agent against a pathogenic disease absorbed therein, so that a mammal biting the composition squeezes the vehicle causing said immunizing agent to be expelled from the vehicle and thereby receives an immunizing dose of said immunizing agent.

16. The method of claim 15 wherein said baited composition is set out by aerial distribution of a plurality of individual ones of said composition in a geographical area frequented by the mammals.

17. The method of claim 16 wherein said mammals are a wildlife population.

18. The method of claim 17 wherein the wildlife population includes carnivores.

19. The method of claim 18 wherein the carnivores include foxes.

20. The method of claim 19, wherein the immunizing agent is a rabies vaccine.

21. The method of claim 15 wherein said mammals are dogs.

22. The method of claim 21 wherein said immunising agent is a rabies vaccine.

* * * * *